US00PP28238P2

(12) United States Plant Patent
Korlipara

(10) Patent No.: US PP28,238 P2
(45) Date of Patent: Aug. 1, 2017

(54) ***GEUM* PLANT NAMED 'TNGEURO'**

(50) Latin Name: ***Geum* hybrid**
Varietal Denomination: TNGEURO

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,757

(22) Filed: Jun. 22, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Klarquist Sparkman, LLP

(57) ABSTRACT

A new and distinct *Geum* plant named 'TNGEURO' characterized by red-orange flower color, heavy flowering, dense, deep green foliage with large attractive leaves, a compact, mounding habit, long bloom time, and excellent vigor.

1 Drawing Sheet

Botanical designation: *Geum* hybrid.
Variety denomination: 'TNGEURO'.

BACKGROUND OF THE INVENTION

The present invention relates to a new and distinct cultivar of *Geum* plant given the name 'TNGEURO'. *Geum* is in the family Rosaceae. The new cultivar was bred using unknown, unnamed proprietary plants. The new cultivar was selected for its superior habit and flowering.

Compared to *Geum* 'Fire Storm' (U.S. Plant Pat. No. 23,179), the new cultivar is much more compact and the flowers are single to semi-double rather than double.

Compared to *Geum* 'Totally Tangerine' (U.S. Plant Pat. No. 22,041), the new cultivar has a more compact habit, shorter flowering stems, a longer bloom time, and darker orange flowers.

Compared to *Geum coccineum* 'Koi' (unpatented), a seed mix, the new cultivar has a bigger habit with more crowns and flowers.

SUMMARY OF THE INVENTION

The following traits have been repeatedly observed and are determined to be the unique characteristics of 'TNGEURO'. These characteristics in combination distinguish 'TNGEURO' as a new and distinct cultivar:

1. red-orange flower color,
2. heavy flowering,
3. dense, deep green foliage with large attractive leaves,
4. compact, mounding habit,
5. long bloom time, and
6. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a three-year-old *Geum* 'TNGEURO' growing in the field in Canby, Oreg.

FIG. 2 shows a one-year-old *Geum* 'TNGEURO' in a one gallon container outside in April in Canby, Oreg.

DETAILED PLANT DESCRIPTION

The following is a detailed description of the new *Geum* cultivar based on observations of a 1 and a half year old specimens growing in the field full sun under typical outdoor conditions in May in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 2007, 5$^{th}$ edition.

Plant:

*Type*.—Herbaceous perennial.
*Hardiness*.—USDA Zone 5-9.
*Size*.—30 cm wide and 22 cm tall to top of the foliage, 40 cm to top of flowers.
*Form*.—Mound with 20 to 30 crowns.
*Vigor*.—Excellent.
*Stem*.—None.

Leaf:

*Type*.—Simple, rosulate.
*Arrangement*.—Rosette.
*Surface texture*.—Pubescent on both sides.
*Venation*.—Pinnate and impressed.
*Petiole and rachis*.—Grows to 18 cm long and 2.5 wide (5 mm wide at base), pubescent, Yellow Green 144A, petiole base clasping.

*Rosulate leaves*.—Lyrate-pinnate, 5-foliate with very small leaflets in pairs below leaflets (to 5 mm wide, 7 mm long), terminal leaflet largest, rhomboid, grows to 7.5 cm long and 11.5 cm wide, 7 lobed, often cupped at base, cordate base, margins irregularly serrate, tip obtuse to notched to acute; top lateral leaflets, 3.5 cm long and 2.5 cm wide, irregularly obovate, with 2 lateral shallow lobes, margins serrate, opposite, cupped, tips acute, bases cuneate, sessile.

*Color*.—Topside Green 137A including veins, bottom side Yellow Green 146B with veins 146C.

Inflorescence:

*Description*.—In cymes, about 3 cymes from each rosette with 2 to 7 flowers per cyme.

*Size of inflorescence*.—Grows to 9 cm wide and 15 mm deep.

*Flowering stem attitude*.—Upright.

*Peduncle*.—Grows to 18 cm tall and 4 mm wide, pubescent, Yellow Green 147C where shaded and Greyed Purple 187A where exposed to sun.

*Peduncle leaves*.—Lyrate, sessile, grow to 6 cm long and 3 cm wide, 3 to 5-lobed, grow to 8.5 cm long and 7 cm wide, serrate, tips attenuate, base cuneate, pubescent on both sides; stipules large adnate to petiole, foliar, grow to 5 cm long and 3 cm wide, irregularly incised, pubescent on both sides, Yellow Green 146B; leaves and stipules topside Green 137A including veins, bottom side Yellow Green 146B with veins 146C.

*Pedicel*.—Variable in length, 2 cm to 10 long and 1 mm wide, Greyed Purple 187B.

Flower bud:

*Size*.—15 mm long and 11 mm wide.

*Shape*.—Conic, nodding.

*Surface*.—Pubescent.

*Color*.—Greyed Purple 187B.

Flower:

*Type*.—Actinomorphic, single to semi-double.

*Size*.—32 mm wide and 10 mm deep.

*Flower attitude*.—Side-facing.

*Corolla description*.—5 to 8 petals, widely obovate in shape, grows to 12 mm deep and 17 mm wide, margins entire, tip obtuse to slightly notched, base truncate, glabrous on both sides, top side Orange Red 35A, bottom side Orange Red 31C.

*Calyx description*.—5 sepal lobes, stellate, 4 mm deep and 28 mm wide, Yellow Green 148B inside, Yellow Green 148C tinted Greyed Purple 187A on outside, pubescent outside and glabrous inside, lobes ovate, flattened to tube, margins entire, tips acuminate, each lobe 6 mm long and 5.5 mm wide.

*Pistil description*.—1 in number, 6 mm long and 6 wide, ovary 4 mm long and 5 mm wide, Yellow Green 146C and covered with white hairs; about 100 hair-like styles and stigmas, styles 6 mm long, Orange 28C; stigmas Greyed Purple 187A.

*Stamen description*.—About 160, 5 mm long, filaments 4.5 mm long, Orange 24B, anthers 0.5 mm long, Orange 24A, pollen Yellow Orange 18A.

*Fragrance*.—None.

*Lastingness*.—Each flower last approximately one week in summer and up to two weeks in cool weather.

*Bloom time*.—April to June.

Fruit: None.

Seed: None, sterile.

Disease and pests: The new cultivar is typical to the genus. No known resistances to pests or diseases.

I claim:

1. A new and distinct *Geum* plant as herein illustrated and described.

* * * * *

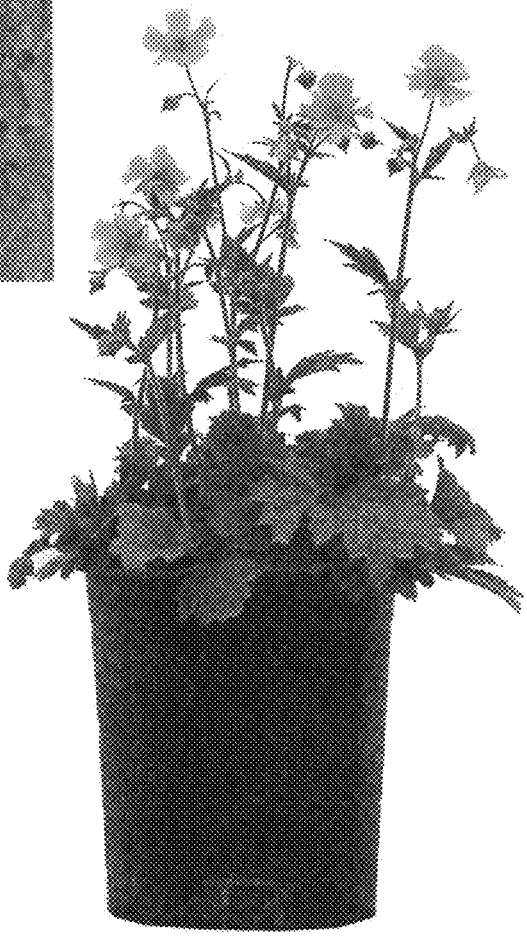

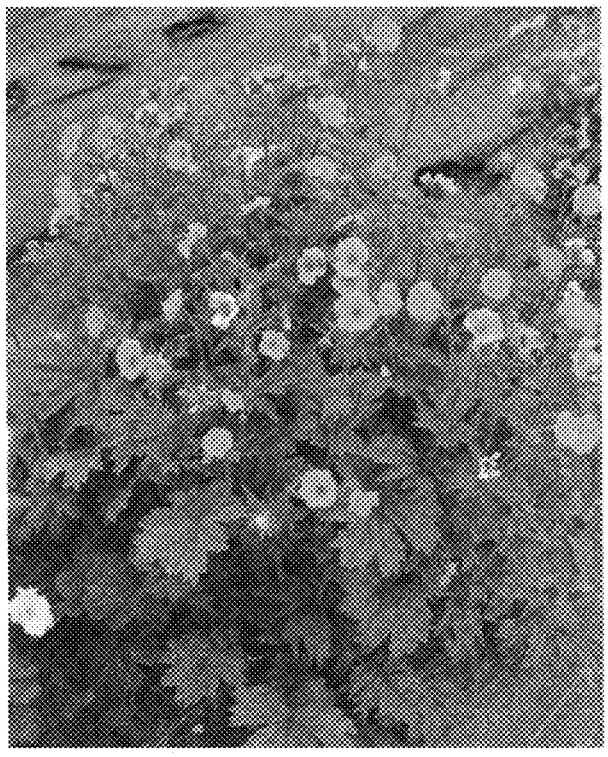
FIG. 1 above,
FIG. 2 on right.